(12) United States Patent
Habermeyer et al.

(10) Patent No.: US 7,648,530 B2
(45) Date of Patent: Jan. 19, 2010

(54) HUMERAL HEAD PROSTHESIS

(75) Inventors: Peter Habermeyer, Heidelberg (CH); Peter Kälin, Unterägeri (CH)

(73) Assignee: SQ Products AG, Steinhausen (CH)

( * ) Notice: Subject to any disclaimer, the term of this patent is extended or adjusted under 35 U.S.C. 154(b) by 0 days.

(21) Appl. No.: 10/586,459

(22) PCT Filed: Jan. 13, 2005

(86) PCT No.: PCT/CH2005/000011

§ 371 (c)(1),
(2), (4) Date: Aug. 2, 2007

(87) PCT Pub. No.: WO2005/070345

PCT Pub. Date: Aug. 4, 2005

(65) Prior Publication Data

US 2007/0282450 A1 Dec. 6, 2007

(51) Int. Cl.
*A61F 2/40* (2006.01)
(52) U.S. Cl. .................. 623/19.11; 623/19.13
(58) Field of Classification Search ... 623/19.11–19.14; A61F 2/40
See application file for complete search history.

(56) References Cited

U.S. PATENT DOCUMENTS

| 6,736,852 | B2 * | 5/2004 | Callaway et al. | 623/19.14 |
|---|---|---|---|---|
| 7,097,663 | B1 * | 8/2006 | Nicol et al. | 623/19.13 |
| 7,166,132 | B2 * | 1/2007 | Callaway et al. | 623/23.47 |
| 7,204,854 | B2 * | 4/2007 | Guederian et al. | 623/19.11 |
| 2003/0050704 | A1 * | 3/2003 | Keynan | 623/22.12 |
| 2003/0149485 | A1 * | 8/2003 | Tornier | 623/18.11 |
| 2004/0059424 | A1 * | 3/2004 | Guederian et al. | 623/19.11 |
| 2004/0225367 | A1 | 11/2004 | Glien et al. | |
| 2005/0278030 | A1 * | 12/2005 | Tornier et al. | 623/19.11 |

FOREIGN PATENT DOCUMENTS

| DE | 101 23 517 C1 | 11/2002 |
|---|---|---|
| EP | 0 664 108 A2 | 7/1995 |
| EP | 1 125 565 A2 | 8/2001 |
| GB | 2 007 980 A | 5/1979 |
| WO | WO 03/051238 A1 | 6/2003 |

OTHER PUBLICATIONS

International Search Report; PCT/CH2005/000011; Jan. 13, 2005.
International Preliminary Report on Patentability; International Application No. PCT/CH2005/000011; International Filing Date: Jan. 13, 2005.

* cited by examiner

*Primary Examiner*—Corrine M McDermott
*Assistant Examiner*—Jason-Dennis Stewart
(74) *Attorney, Agent, or Firm*—Antonelli, Terry, Stour & Kraus, LLP.

(57) ABSTRACT

A shoulder joint prosthesis has an at least two-pieced humeral head prosthesis, comprising a calotte, or a joint head (3) and a fixing body (5, 7). The latter comprises a fixing piece (15), for detachable connection of the calotte and a mounting section (21), for the at least cement-free anchoring of the fixing device in the bone. The fixing body is preferably of two-piece embodiment, comprising a discoid positioning body (5) with a medial hole and an anchoring body (7), provided for fixing the positioning body (5) to the bone through the medial hole (19).

7 Claims, 2 Drawing Sheets

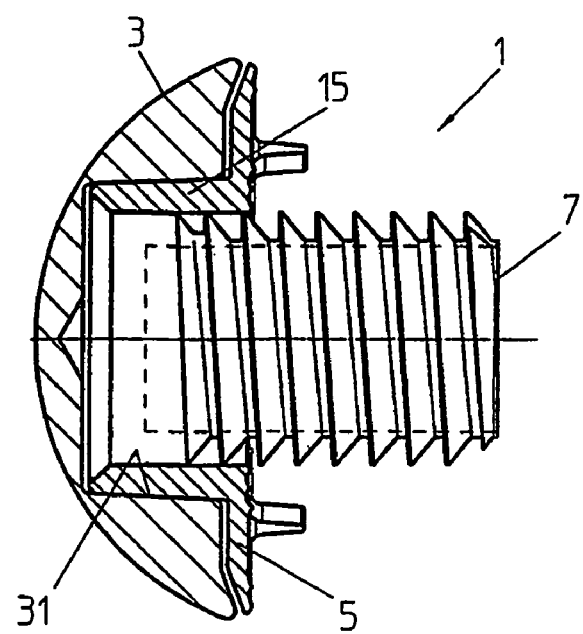
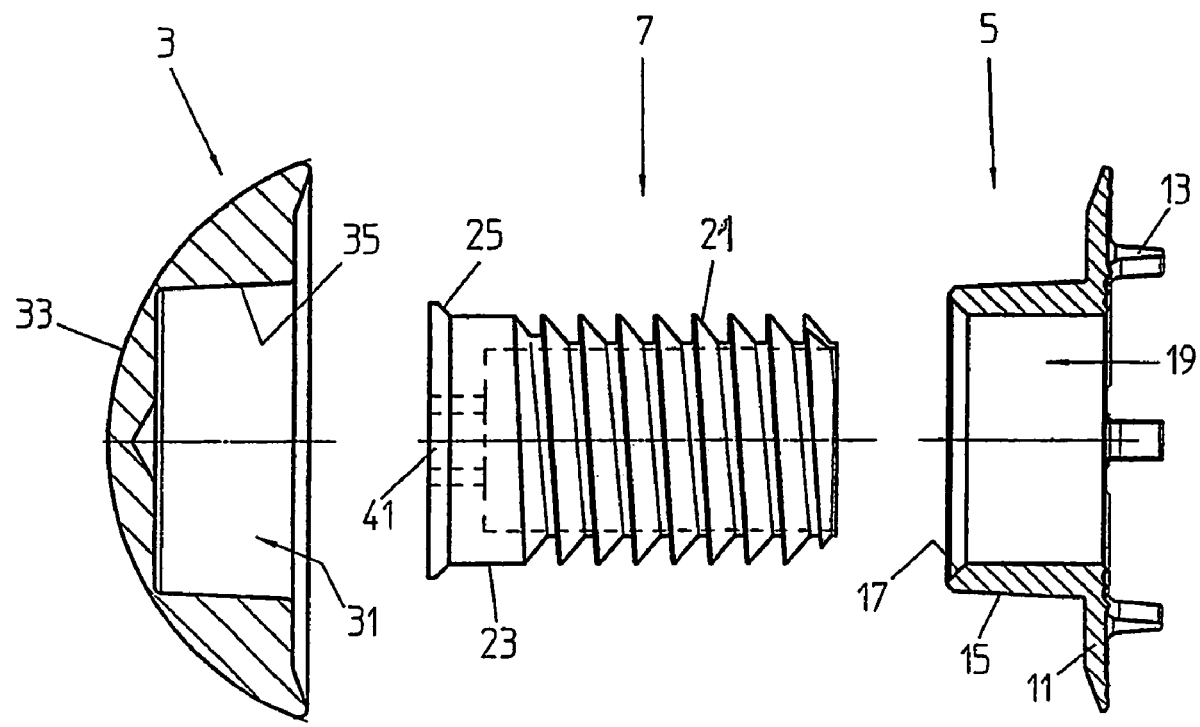

HUMERAL HEAD PROSTHESIS

RELATED APPLICATION

This application is a U.S. national stage filing under 35 U.S.C. §371 of International Application No. PCT/CH2005/000011 filed Jan. 13, 2005 and claiming priority under 35 U.S.C. §119 of Switzerland patent application no. 82/04 filed Jan. 22, 2004.

TECHNICAL FIELD

The invention relates to a shaftless shoulder joint prosthesis, and to a method of fitting a shoulder joint prosthesis.

BACKGROUND

Particularly in the case of young patients, or patients in whom the bone substance is well preserved, care must be taken that as little bone substance as possible is lost when fitting a shoulder prosthesis. Another important requirement is that mobility be preserved, while at the same time maintaining joint stability.

Already known in this regard are so-called cup shoulder prostheses which are offered by, among others, the companies Centerpulse and Biomet Orthopedics. With these so-called cup shoulder prostheses, the head component is fixed to the joint head bone, with or without bone cement, by means of a shaft located medially within a cap-like head. Accessibility to the joint socket is thus significantly impeded due to the fact that the joint head is essentially maintained. As a result, the necessary socket-restorative appliance is omitted.

SUMMARY OF INVENTION

The goal of the invention is therefore to propose a humeral head or shoulder joint prosthesis which is especially well-suited both for fitting a joint socket as well as providing a cement-free replacement of the joint head for patients with well-preserved bone substance. According to the invention, the goal proposed is achieved by a shoulder joint prosthesis comprising an at least two-piece humeral head prosthesis, composed of a calotte or joint head, and an attachment body, including an attachment part for the mounting attachment of the calotte, as well as a mounting segment to effect an at least cement-free anchoring of the attachment body within the bone.

In contrast to the known so-called cup shoulder prostheses, the invention proposes not to attach the joint head to the humerus or shoulder bone by means of a shaft affixed to the head, but instead to first fit an attachment body onto which the humeral head or joint head is mounted.

The attachment body is preferably designed with at least two parts, consisting of a so-called pressure disk, possibly also termed a positioning disk, and a hollow screw by which the disk is fixed on the bone. As a result, in contrast to the cup shoulder prosthesis, in this case no cartilage is removed down to the subchondral bone; instead the entire head along the neck of the humerus is resected. The head replacement, preferably consisting of the aforementioned hollow screw, pressure disk and joint head, is fixed in cement-less fashion by the hollow screw within the humerus. The prosthesis proposed according to the invention is suitable both for hemiprosthetic and also for total joint replacement.

The shaftless humeral head prosthesis according to the invention rests by the aforementioned pressure disk on the surface of resection. The size of the disk is selected such that a complete cortical support is created circumferentially. The pressure disk is thus attached within the spongiosa by the aforementioned hollow screw. As a result, under load an application of force is effected both on the cortical substance and on the spongiosa.

Classical primary shaft prostheses require resection of the humeral head along the anatomical neck. In the case of the shaftless humeral prosthesis proposed according to the invention, resection is also performed at this site. In the event of any subsequent revision surgery, this feature allows for later use of a classical primary shaft prosthesis without resectional corrections.

In contrast to the aforementioned cup prostheses known from the prior art, it is evident that the joint head cap extends down below the anatomical neck. In the event of an expansion of the cap, the resection must be effected below the anatomical neck, and this goes too deep to allow fitting of classical shaft prostheses.

Another advantage of the shaftless humeral head prosthesis proposed according to the invention is that implantation is possible independently of the geometry of the humeral shaft. Especially in the case of previous humeral fractures, a displacement of the fractured head calotte relative to the humerus often occurs. Here the humerus is often shifted in the anterior and medial direction, while the head segment is displaced in the posterior and lateral direction. The ability to use conventional shaft prostheses can then be significantly hampered since introduction of the shaft into the bone marrow space is impeded by the offset and the medial offset may be too large.

Finally, what must be mentioned as advantages of the shaftless humeral head prosthesis proposed according to the invention are the relatively simple manipulation and reliable and proven cement-free anchoring by means of the hollow screw proposed according to the invention. In addition, it is possible to provide a wide array of implant sizes, thereby enabling the anatomically correct restoration of the joint by means of the modular design.

The following explains the invention in greater detail by means of examples and with reference to the attached drawings:

BRIEF DESCRIPTION OF DRAWINGS

FIG. 4 shows a longitudinal section through a humeral head prosthesis according to the invention, and;

FIG. 5 is a longitudinal cross-section through the prosthesis of FIG. 4 in the disassembled separated state.

DETAILED DESCRIPTION

Figure 1:
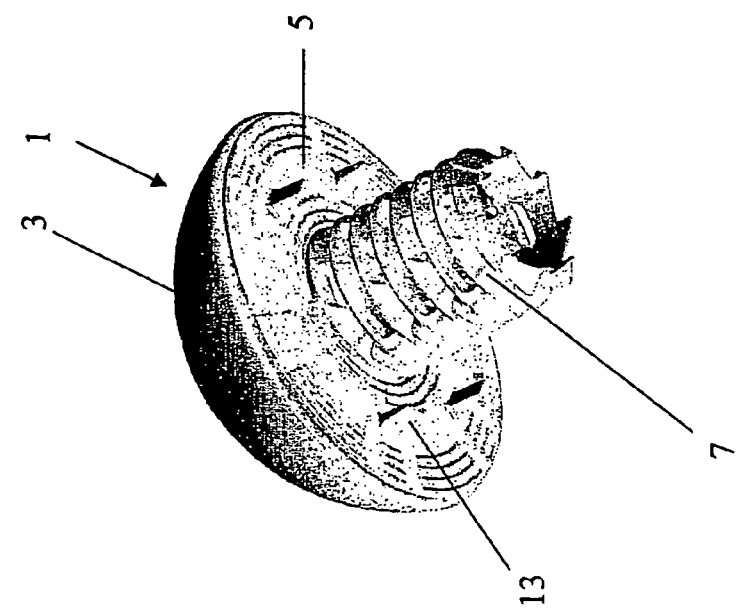
FIG. 1 is a perspective view illustrating a shaftless humeral head prosthesis according to the invention in the assembled state.

FIG. 1 is a perspective view illustrating a humeral head prosthesis 1 according to the invention seen laterally from below, including a joint head 3 which is mounted on a pressure disk 5 and is essentially abutting this disk. A hollow screw 7 is fitted so as to project medially through pressure disk 5, said screw being provided in order to affix joint head 3 along with pressure disk 5 within or on the bone. Also seen are the downward-protruding fixation hooks or lugs 13 which rotationally fix the pressure disk to the bone.

Figure 2:
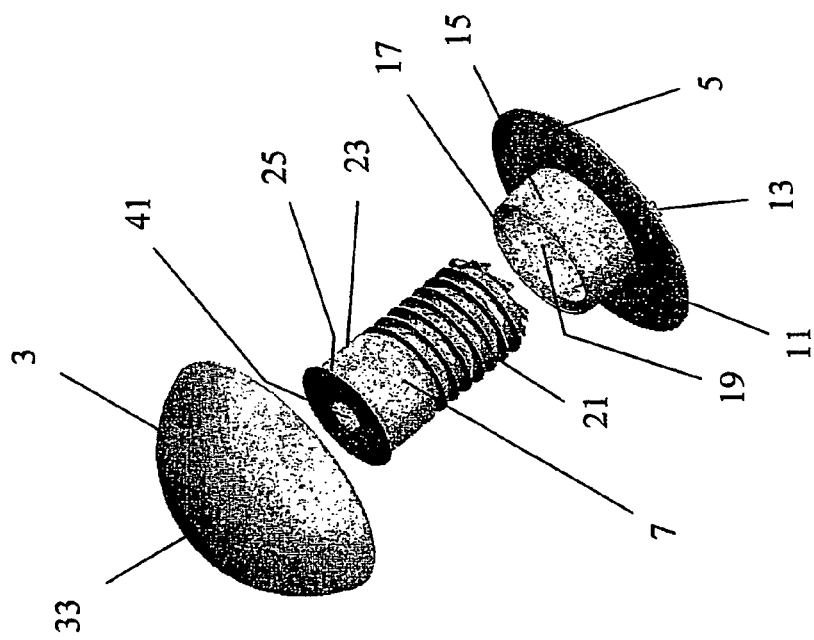
FIG. 2 is a perspective view illustrating the prosthesis of FIG. 1 in a disassembled state.

FIG. 2 is another perspective view of the prosthesis of FIG. 1—illustrating it, however, when disassembled into individual components. Evident here is joint head 3 including the at least nearly spherical joint surface 33. Hollow screw 7 has a thread 21 with which to fix the hollow screw within the bone. For this purpose, hollow screw 7 is driven into the bone through a medial hole 19 of pressure disk 5. In addition, hollow screw 7 has one at least essentially smooth-walled shaft 23, the inside of which comes to rest on collar 15 projecting from pressure disk 5 when hollow screw 7 is screwed into the bone. A retaining flange 25 is located on the end of hollow screw 7 and is beveled so as to rest on a similarly beveled or conically-shaped support edge 17 on the end of collar 15.

Finally, what is shown is pressure disk 5 with an annular-shaped section 11, on the bottom of which the aforementioned fixation hooks 13 are located.

Figure 3:
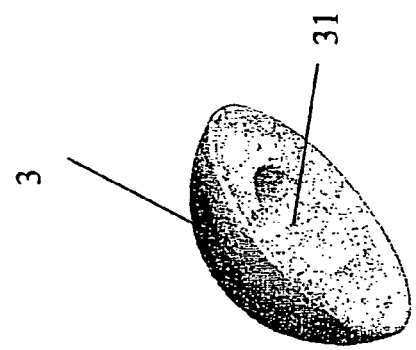
FIG. 3 is a perspective view illustrating the joint head of FIG. 2—however rotated so that the side opposite the joint head is visible.

FIG. 3 is a perspective view illustrating joint head 3—rotated, however, relative to the view of FIG. 2 so as to be visible from the bottom. A receiver 31 of a hollow cone design is clearly visible which serves to receive the collar-like projection 15 of pressure disk 5.

FIG. 4 is a longitudinal view of the humeral head prosthesis defined according to the invention which clearly shows how the flange or collar 15 of positioning or pressure disk 5 is fitted within hollow-cone-shaped receiver 31 of joint head 3.

Finally, FIG. 5 again illustrates the joint prosthesis according to the invention when disassembled or in the separated state so as to show the three individual components. FIG. 5 clearly shows that the end support edge of collar 15 is of a conical or beveled shape, as is analogously the end retaining flange 25 projecting laterally from hollow screw 7. This conical or beveled design ensures the positionally correct insertion of hollow screw 7 into the medial hole 19 of pressure disk 5. Also evident is the fact that collar 15 of disk 5 as well is slightly beveled or conically shaped, as is the inner wall 35 of round receiver 31 as well, in order to provide secure mounting of joint head 3 over collar 15 of disk 5. It has been found in practice that during the mounting process joint head 3 can be affixed by means of a slight tap on the joint head such that subsequent detachment becomes impossible when the humerus is moved.

Fitting the prosthesis according to the invention is quite simple per se in that first the positioning or pressure disk 5 is applied to or positioned on the previously prepared bone. A provisional positionally-correct fixation of the disk to the bone is enabled by the downward-protruding projections or hooks 13. Hollow screw 7 is now screwed through medial hole 19, whereby this step can be effected, for example, using a so-called hex key which medially engages an end hole 41 of hollow screw 7.

After hollow screw 7 has been screwed in such that retaining flange 25 rests on conical support edge 17, joint head 3 can now be fitted by placing this head over collar 15. In order to effect definitive fixation, it is finally necessary, for example, to apply a light tap to the outer joint contour 33.

The prosthesis according to the invention shown in reference to FIGS. 1 through 5 is of course simply one example which can be altered, modified, or augmented by additional elements using any number of approaches. In particular, the illustration relates simply to the joint head prosthesis, while illustration of the corresponding joint socket was dispensed with since joint sockets are extremely well known in the field of prosthesis construction. For example, it is possible analogously to fit a joint socket, for example, on a shoulder bone by an approach in which a joint socket can be attached within the scapula or shoulder blade bone by a conical component and hollow screw. Similarly, the selection of material for fabricating a joint head according to the invention is not addressed per se by the present invention. By way of example, cobalt-chromium-based alloys are employed. For example, metal alloys based on titanium are well suited for the remaining components of the prosthesis according to the invention. In addition, the geometry of the prosthesis according to the invention is also not addressed per se by the present invention since this must either be adapted to the specific conditions of the given shoulder joint, and in any case is preferably of an essentially spherical design. In this regard, it is advantageous according to this invention that the joint head, or the surface thereof, be less than hemispherical in form so as to simplify both manipulation as well as any subsequent replacement.

The materials of the attachment bodies are also known per se, such as, for example, alloys based on titanium. Fundamentally, the dimensions of the individual components such as the humeral head itself and the associated joint socket can be altered or varied, and the materials employed for the prosthesis can be adapted appropriately to requirements and to new developments in the science of materials.

The invention claimed is:

1. A shaftless shoulder joint prosthesis, comprising an at least two-piece humeral head prosthesis, composed of a joint head mountable solely on the prosthesis by a tap-on fit, and an attachment body of an at least two-part design including an attachment part for the mounting attachment of the calotte, as well as a mounting segment to effect an at least cement-free anchoring of the attachment body within the bone, wherein the attachment part is a disk-like positioning body having a medial hole about an axis of the body with a relatively large diameter annular-shaped section about the medial hole and axis, a first side of the annular-shaped section having fixation hooks or projections thereon to provide a provisional positionally-correct fixation to a pretreated bone, and a second side of the annular-shaped section opposite said first side having a relatively smaller diameter at least nearly circular, upstanding projecting collar about the medial hole and axis, the collar projecting outwardly from the second side of the annular-shaped section with an inner surface configured to position the mounting segment when effecting said anchoring and an external surface configured for engagement with and attachment of the joint head thereon solely by means of a tap on the joint head, and as said mounting segment an anchoring body having a hollow screw provided in order to affix the positioning body to the bone through the medial hole in the projecting collar and the annular-shaped section.

2. Prosthesis according to claim 1, wherein the joint head has at least one nearly spherical surface corresponding to a spherical section with an opening angle of <180°.

3. Prosthesis according to claim 1, wherein the at least nearly circular projecting collar of the disk-like positioning body has a terminally located, conical support edge, and wherein a beveled retaining flange is formed on the hollow screw of the anchoring body terminally projecting outward to match the support edge so as to rest on or abut the support edge inside the collar.

4. Prosthesis according to claim 3, wherein the joint head has an at least nearly hollow-cylinder-shaped receiver on the side opposite the nearly spherical surface for engaging the external surface of the collar to mount the joint head on the attachment body.

5. Prosthesis according to claim 4, wherein the wall of the hollow-cylinder-shaped receiver and the external surface of the collar of the disc-like positioning body are of a slightly conical or beveled design so as to provide a form-locking and positionally correct mounting of the joint head over the collar.

6. Method of fitting a shaftless shoulder joint prosthesis comprising an at least two-piece humeral head prosthesis, composed of a joint head mountable solely on the prosthesis by a tap-on fit, and an attachment body of an at least two-part design including an attachment part for the mounting attachment of the calotte, as well as a mounting segment to effect an at least cement-free anchoring of the attachment body within the bone wherein the attachment part is a disk-like positioning body having a medial hole about an axis of the body with a relatively large diameter annular-shaped section about the medial hole and axis, a first side of the annular-shaped section having fixation hooks or projections thereon to provide a provisional positionally-correct fixation to a pretreated bone and a second side of the annular-shaped section opposite said first side having a relatively smaller diameter at least nearly circular, upstanding projecting collar about the medial hole and axis, the collar projecting outwardly from the second side of the annular-shaped section with an inner surface configured to position the mounting segment when effecting said anchoring and an external surface configured for engagement with and attachment of the joint head thereon solely by means of a tap on the joint head, and as said mounting segment an anchoring body having a hollow screw provided in order to affix the positioning body to the bone through the medial hole in the projecting collar and the annular-shaped section, said method comprising fitting the attachment body of the prosthesis on a previously prepared humerus without use of cement, and then fitting the joint head of the prosthesis on the attachment body, wherein said step of fitting the attachment body on the previously prepared humerus includes attaching the disk-like positioning body as said attachment part at a predetermined position to the prepared bone, wherein a provisional positionally-correct fixation is provided by the hooks or projections protruding from the positioning body, after which the positioning body is anchored or fixed to the bone by the hollow screw of said mounting segment which is inserted through the medial hole in the projecting collar and the annular-shaped section of the positioning body, and tapping on the joint head to form a tap-on fit between the joint head and the external surface of the collar for attaching the calotte on the attachment body of the prosthesis fixed to the bone.

7. Method according to claim 6, wherein the external surface of the at least nearly circular projecting collar is slightly conically-shaped and the joint head is fitted on the fitted attachment body with the slightly conically-shaped collar protruding from the bone by an approach in which a hollow-cylinder-shaped receiver on the inside of the joint head, which receiver also has a slightly conically-shaped wall, is mounted in a form-locking manner over the collar; and that finally the joint head is definitively fastened or fixed by applying a force to its external surface to form said tap-on fit.

* * * * *